(12) United States Patent
Johanson

(10) Patent No.: US 9,182,333 B2
(45) Date of Patent: *Nov. 10, 2015

(54) DEVICE AND METHOD TO MEASURE BULK UNCONFINED PROPERTIES OF POWDERS

(71) Applicant: Johanson Holdings LLC, Gainesville, FL (US)

(72) Inventor: Kerry Johanson, Gainesville, FL (US)

(73) Assignee: JOHANSON HOLDINGS LLC, Gainesville, FL (US)

(*) Notice: Subject to any disclaimer, the term of this patent is extended or adjusted under 35 U.S.C. 154(b) by 53 days.

This patent is subject to a terminal disclaimer.

(21) Appl. No.: 13/718,565

(22) Filed: Dec. 18, 2012

(65) Prior Publication Data

US 2013/0220038 A1  Aug. 29, 2013

Related U.S. Application Data

(63) Continuation-in-part of application No. 13/403,363, filed on Feb. 23, 2012, now Pat. No. 8,355,129, which is a continuation of application No. PCT/US2010/045265, filed on Aug. 12, 2010.

(60) Provisional application No. 61/237,648, filed on Aug. 27, 2009.

(51) Int. Cl.
*G01N 21/84* (2006.01)
*G01N 19/00* (2006.01)
*G01N 3/00* (2006.01)
*G01N 21/03* (2006.01)

(52) U.S. Cl.
CPC ............ *G01N 19/00* (2013.01); *G01N 3/00* (2013.01); *G01N 2021/0339* (2013.01); *G01N 2203/0284* (2013.01); *G01N 2203/0641* (2013.01)

(58) Field of Classification Search
CPC .......... G01N 19/00; G01N 2021/0339; G01N 21/85; G01N 11/00; G01N 11/02
USPC .............................................. 356/426; 73/866
See application file for complete search history.

(56) References Cited

U.S. PATENT DOCUMENTS

| | | | |
|---|---|---|---|
| 3,468,167 A | | 9/1969 | Martinek et al. |
| 3,638,478 A | * | 2/1972 | Dietert et al. ................. 73/73 |
| 3,665,768 A | * | 5/1972 | Hosokawa et al. ............ 73/866 |
| 4,181,023 A | * | 1/1980 | Clamroth et al. .............. 73/866 |
| 4,274,286 A | * | 6/1981 | Gioia ............................. 73/866 |
| 5,109,717 A | | 5/1992 | Galetto et al. |
| 5,117,699 A | | 6/1992 | Johanson |
| 5,627,308 A | * | 5/1997 | Dahneke ..................... 73/28.01 |
| 5,847,294 A | | 12/1998 | Poole |
| 6,049,388 A | | 4/2000 | Masterson et al. |
| 7,767,370 B2 | * | 8/2010 | Ishigami et al. ......... 430/45.51 |
| 2007/0107540 A1 | | 5/2007 | Davies |

* cited by examiner

*Primary Examiner* — Tarifur Chowdhury
*Assistant Examiner* — Isiaka Akanbi
(74) *Attorney, Agent, or Firm* — Sven W. Hanson

(57) ABSTRACT

A method testing physical properties of bulk powder materials uses acceleration forces induce a change in physical configuration of a powder sample. Various different properties may be determined by relationships between the applied acceleration and the associated detected change in configuration event. In various embodiments powder strength, friction angle, or other properties may be determined. Novel methods and devices are provided.

14 Claims, 8 Drawing Sheets

DEVICE AND METHOD TO MEASURE BULK UNCONFINED PROPERTIES OF POWDERS

RELATED APPLICATIONS

The present application is a continuing application of pending U.S. application No. 13/403,363 (filed Feb. 23, 2012), which is a continuing application of international application No. PCT/US10/45265, filed Aug. 12, 2010 that claims priority benefit from U.S. Provisional application No. 61/237,648, filed Aug. 27, 2009.

BACKGROUND OF THE INVENTION

The present invention relates to devices and methods to measure bulk unconfined properties, such as yield strength, of powders using minimal material. The traditional method of measuring the bulk strength of a powder is to place material in some form of shearing device that allows a consolidation load to be placed on top of the material. The material is then sheared to bring it to a steady shear load condition measured by load cells. The consolidation load is decreased, and the sample is sheared again to measure the peak shear stress. This procedure is typically repeated five to seven times at different shear loads, and all of this data is used to compute a single measurement of unconfined yield strength. The shear cells utilized to accomplish this task hold between 75 cc (cubic centimeters) and 400 cc material and may require multiple fillings. This prior art procedure is complex and requires a trained technician to perform these tests. These devices generally produce a value that is repeatable to only about 30 percent. Often sufficient material is not available for a detailed analysis using these standard methods. This is especially true in the formulation stage of the product or process design.

The inability to characterize properties such as the bulk cohesive strength of powders using prior methods can lead to significant production losses in pharmaceutical, food, cosmetic, pigment, chemical, and other industries that handle bulk powders. Companies often desire to characterize bulk properties prior to process design, but have insufficient quantities of material to accomplish this by standard means. Failure to characterize the bulk cohesive properties leads to process failure and costly redesigns, extending time-to-market and wasting company resources. In addition, product quality is strongly influenced by the degree of cohesion a bulk powder material possesses. The ability to obtain a measurement of cohesive flow properties early in the design process provides valuable information to guide product development.

What is needed are new precise methods and devices to measure bulk properties such as strength of powder materials, those new methods and devices should require only minimal quantities of powder material and capable of being carried out by relatively low-skilled persons.

SUMMARY OF THE INVENTION

The present invention includes testing devices and methods to determine or measure physical properties of bulk powders using minimal material. In the present inventive method various properties of a bulk powder material can be determined by detecting a defined relationship between externally applied forces applied to the body of a sample volume of bulk powder and a change in the bulk volume configuration of the powder sample as a consequence of the force applied. The change in sample configuration is defined by and is a product of a relative movement of the aggregate particles within the sample volume. This change in configuration may evidence itself in one of a variety of detectable events, including bulk collapse of the unsupported sample, increased density, or relative movement of at least a portion of the sample boundary surface. The particular configuration change or detected event is dependent at least on the specific application, test cell arrangement and powder property to be determined. The various powder material properties determinable through application of the inventive devices and methods includes unconfined yield strength, density and friction angle.

In preferred embodiments a cavity in a rigid test cell is filled with a sample volume of the test powder. The cavity is rotated about a distant axis to induce acceleration forces in the sample until a change in configuration within the sample occurs and is detected. The critical acceleration may be measured or calculated and from the acceleration and other known parameters such as the sample physical boundary conditions, the property of interest may be determined.

In alternative embodiments of the inventive methods, a bulk strength characteristic of powder materials is determined by applying known acceleration forces on a test cell containing unconfined powder. The powder is first consolidated in a test cell cavity to replicate a prescribed condition such as might exist in a process stream of interest. Failure of the powder in testing is determined by its escape from the cavity under acceleration forces. Strength is determined by calculation based on the powder material properties, cavity geometry and acceleration forces at failure. In the associated inventive methods the following steps are performed to accomplish the task of measuring bulk unconfined yield strength of material. First, a quantity of powder material is prepared by passing through a sieve to remove any lumps. A conical hole or cavity in a test cell is then filled with the powder and the cell closed to retain the powder within. The amount of powder in the cell is determined by weight. The powder in the cell is then consolidated by rotating the cell about an axis perpendicular to a cell longitudinal axis, thereby inducing a prescribed packed or stressed state. The ends of the test cells are then exposed and the cell rotated again to generate increasing acceleration forces to drive the powder from the cell. The event of the powder leaving the cell is detected by detecting light passing through the cell cavity—the light previously being blocked by the powder in the cell. The strength of the powder is then calculated from the cell geometry, powder characteristics, and rotation induced acceleration forces at the time of failure of the bulk powder.

Embodiments of the invention may successfully use as little as about 0.1 milliliters of material, a single filling of the cell, to measure the bulk unconfined yield strength or other properties of the powder material. The procedure is simple and requires little operator training to perform. Because the invention is simple and uses little material, it is well suited to characterize bulk strength during product formulation stages and can provide guidance during early stages of product and process design, thereby minimizing the time-to-market for final products such as pharmaceuticals.

Various other embodiments are contemplated and are disclosed or make clear from the following detailed description of the inventive embodiments and associated claims.

DESCRIPTION OF THE EMBODIMENTS

It is commonly known that cohesive arches form in conical hoppers of powders as a result of either the interlocking of powder particles or the net effect of all the adhesive forces between particles. The powder's strength in these circumstances is a measurement of the cohesive nature of the product and is directly proportional to the arching tendency of the material. Strength is also a function of the stress level applied to the bulk material. The inventive methods and device herein provide the ability to determine strengths of powders in the context of these prescribed stresses.

In one embodiment of the invention, centrifugal forces acting on a volume of powder material in a test cell generate stress in the material. The stress level caused by spinning a confined bulk material around an axis is directly proportional to the square of the rotational speed. Thus, if the weight of the material sample, the volume of the test sample, and the rotational speed are known, one can compute the stress on the sample during rotation—and also its strength at failure.

Figure 1:
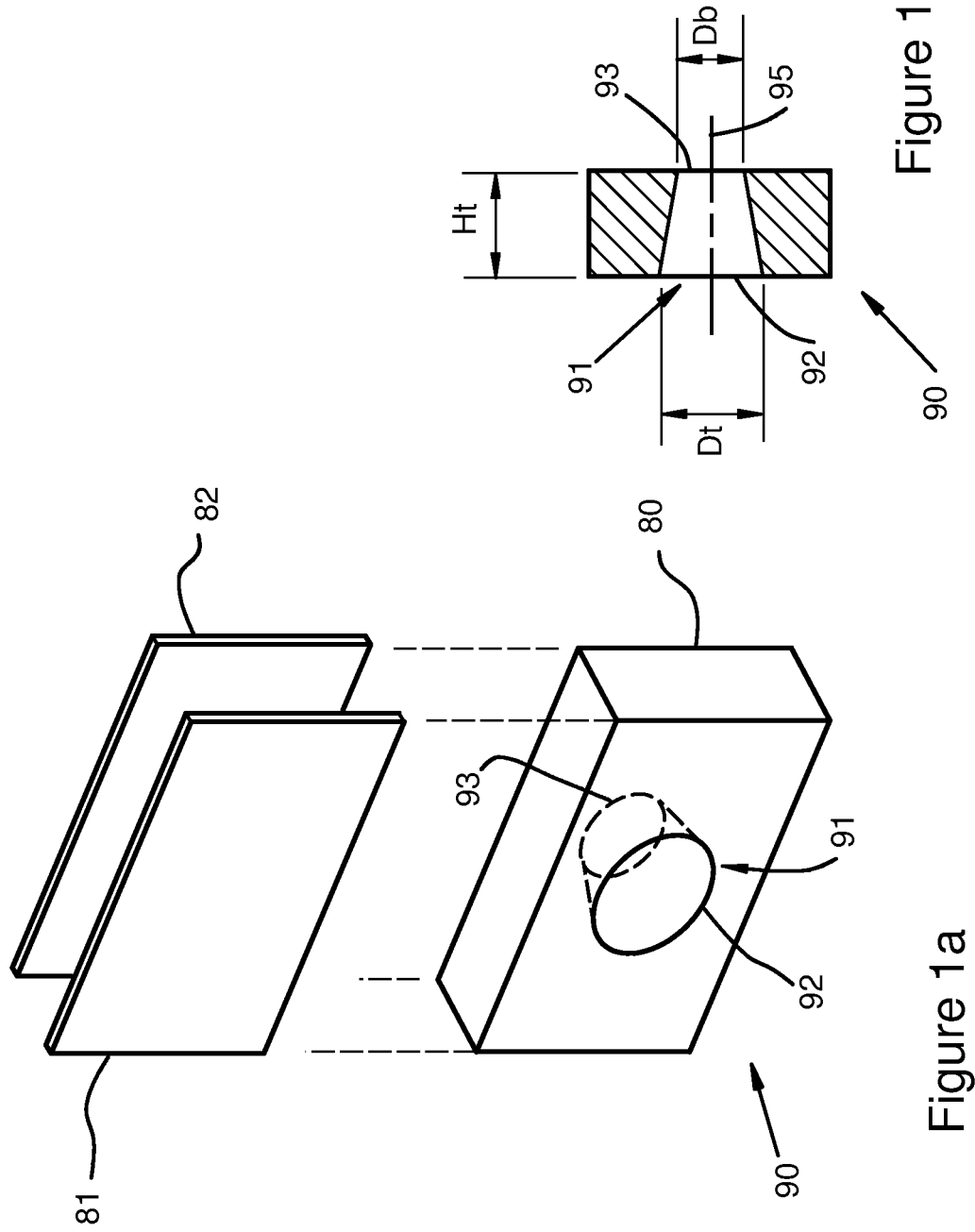
FIG. 1a and 1b illustrate one configuration of a test cell according to the invention.

FIGS. 1a and 1b illustrate a test cell 90 including a cavity 91 according to the invention. FIG. 1b is a cross section view of the cell 90 shown in FIG. 1a (through the center of the cavity 91). Before filling the cell 90, it is important that powder material placed in the cell 90 be free from lumps. The material is preferably prepared by gently pushing the bulk material through a sieve with mesh size three to ten times that of the largest particle in the powder, and the sieved material collected. This has the effect of breaking the lumps and soft agglomerates that may be present in the bulk powder due to caking or other time storage effects.

The cell 90 consists of a conical hole or cavity 91 formed in a body of metal 80. The cavity 91 has a top outlet 92 having a diameter of dimension Dt. For many applications, a diameter dimension Dt of 6.35 millimeters (¼ inch) will be useful. The cavity 91 includes a bottom outlet 93 with a smaller diameter dimension Db that is ⅓ to ½ of the top diameter dimension Dt. The cavity 91 has a height Ht of about 70 percent of the top outlet diameter Dt. The cavity 91 has a conical center axis 95.

Retaining plates 81, 82 hold material in the cell 90 after the cavity 91 is filled. Filling the cavity 90 may be accomplished by placing the bottom plate 82 against and covering the bottom outlet 93 and gently scooping bulk powder into the cell 90. Excess material should be scraped off level with the cell top outlet 92, and the upper plate 81 positioned to cover the top outlet 92. The weight Wt of material in the cell 90 is measured using an external scale accurate to 0.001 grams.

Figure 2:
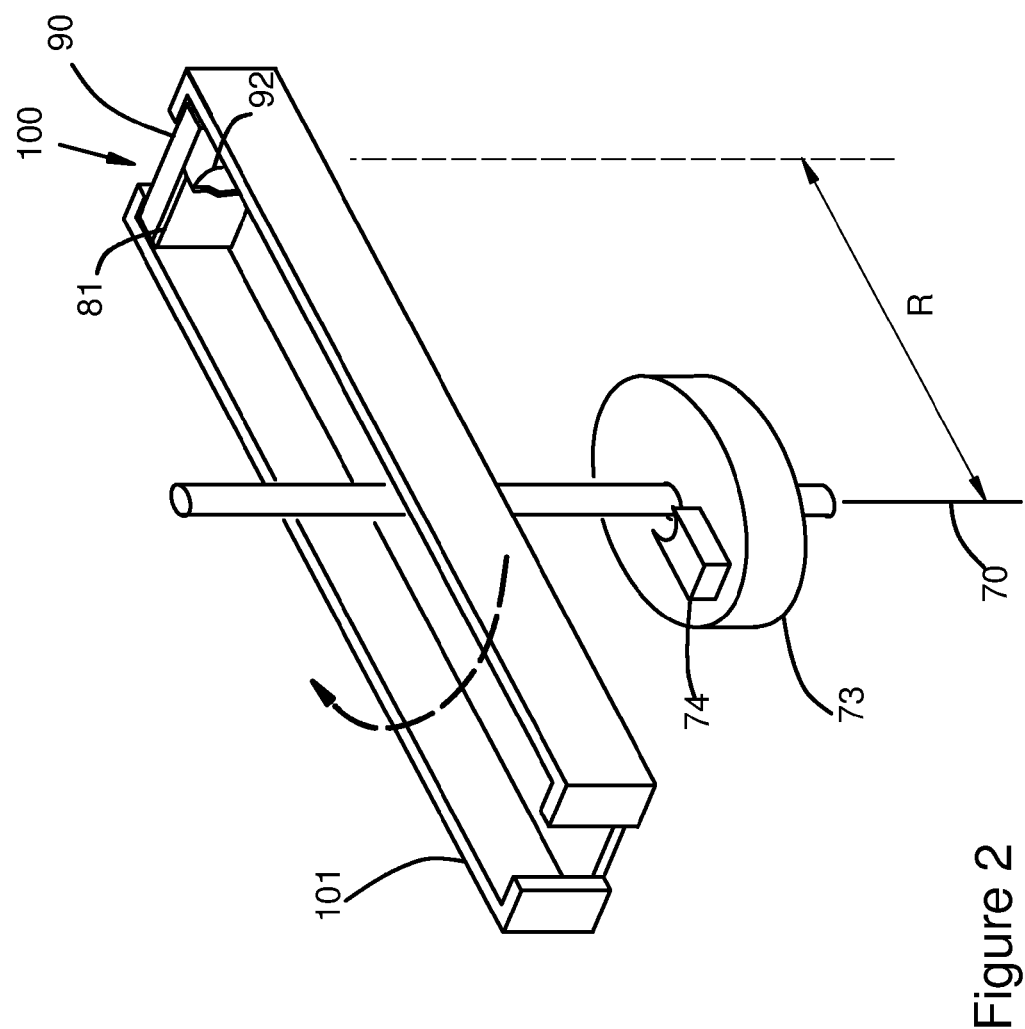
FIG. 2 illustrates a device for rotating a test cell according to the invention for carrying out the test methods.

The material in the cell 90 is then consolidated by placing the cell assembly 100 (consisting of the cell 90 and covers 81, 82) into a rotation arm 101, as shown in FIG. 2, to enable spinning the cell about an axis of rotation 70. For this purpose, the arm 101 may be connected to a conventional motor 73 capable of spinning at high speeds, typically 2,000 to 10,000 RPM (revolutions per minute). The cell is positioned at a distance R from the axis of rotation 70 with the top outlet 92 facing respectively inward and the cavity enter axis 95 perpendicular to the axis of rotation 70 (the top cover 81 is partially cut away in FIG. 2 to display the top opening 92). The arm 101 is rotated slowly, then increasing speed to a prescribed speed (RPMcomp) and then maintained at that speed for a prescribed amount of time. The speed is measured preferably by a non-contact tachometer 74. The motor 73 and tachometer 74 are shown schematically, and the particular appropriate selection, mounting, and operation of these devices will be clear to one skilled in these devices.

The centrifugal (outward) forces caused by rotation of the bulk mass at high speed in a confined geometry cause the material to consolidate and develop stresses within the powder as discussed above.

The consolidation stresses (Sigma) can be calculated by the following equation:

$$\text{Sigma} = 2 \times (2\pi \times \text{RPM}_{comp})^2 \times R \times \text{Density} \times H_t$$

Where Density is a mass density with appropriate units and the remaining parameters are as described above. This equation can be used to determine the prescribed RPMcomp for the purposes of testing for a stress state in a particular application of interest where strength data for the powder is useful. It will be obvious to one skilled in the art that useful prescribed parameters may vary with powder characteristics as well as environmental characteristics.

After consolidation, the top and bottom retaining plates 81, 82 are removed from the cell 90. With the plates 81, 82 removed, the material is free to flow from the outlet once acceleration force is again applied to the powder. If the material possesses strength as a consequence of consolidation induced stresses, the powder will arch over the conical outlet 93 and will not fall out when at rest.

Figure 3:
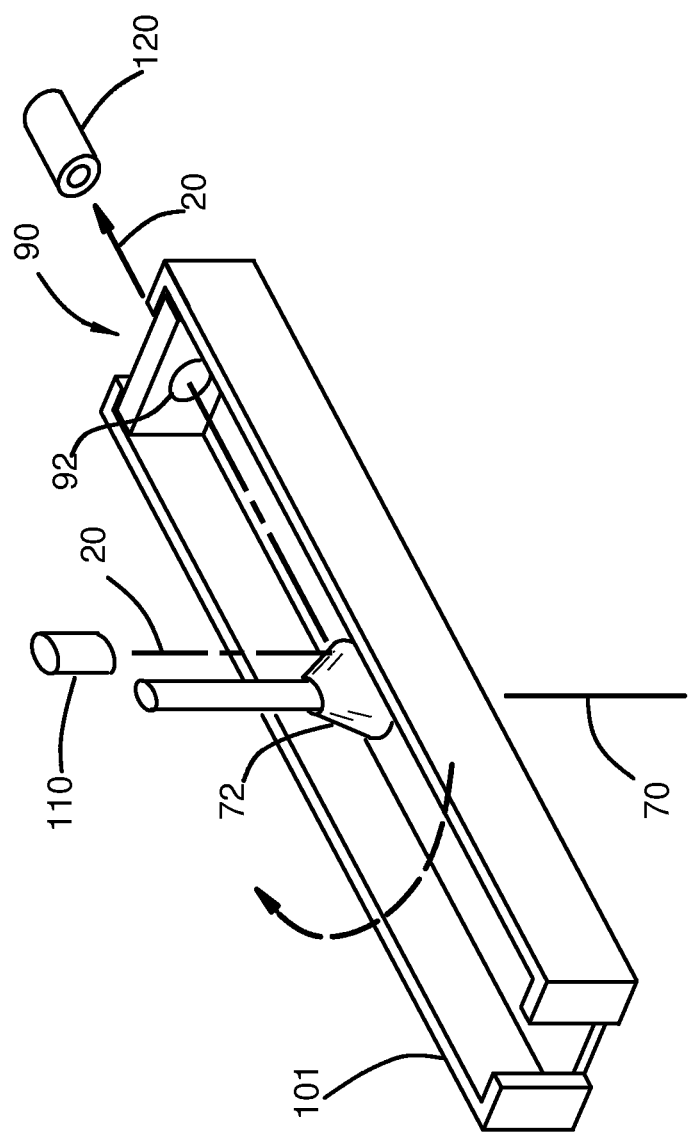
FIG. 3 illustrates a light source and path for detecting failure of powder in a test cell in particular embodiments of the invention.

As shown in FIG. 3, a light source 110 is configured to direct light 20 at the cavity 91. A photosensitive sensor 120 is located on the opposite side of the cell 90 and in line with the bottom opening 93 such as to receive the light 20 if passing through the cavity 91. After consolidation, the material in the cavity 91 blocks the light 20. Thus, light 20 impinging on the sensor 120 indicates that the cavity is no longer blocked by material. In the embodiment shown, the light is reflected for convenience from a conical surface 72 attached to the rotation arm 101 to align the light 20 with the cavity, while allowing the light source 110 to be distant.

During testing for strength, the light 20 is maintained. The cell 90 is then rotated at ever increasing speeds until the forces and stress levels generated by centrifugal acceleration overcome the strength of the bulk material and force material through the outlet 93. When this occurs, the light 20 passes through the outlet 93 to be detected by the photosensitive sensor 120, indicating failure of the cohesive arch in the test cell. The rotational speed at which the light first appears through the cell outlet 93 is recorded as the failure rotation speed (RPMfail). This value is used to compute the bulk strength of the material. The failure stresses can be computed to determine the bulk cohesive strength of the material sample.

The bulk unconfined yield strength (Strength) are calculated from the equation shown below.

$$\text{Strength} = (2\pi^2 Dt^2 R \times \text{Density} \times \text{RPM}_{fail}^2)/(Db \times \cos\phi)$$

Where φ (phi) is the conventional internal angle of friction which can be taken as approximately 30 degrees for most materials and circumstances. If a more accurate value for angle of friction is known in any particular instance, it may be applied in the equation.

The particular design of the rotation arm 101 and structures supporting the cell 90, light source 110 and sensor 120 and the reflective elements directing the light 20 are not critical and various alternatives will become clear to those skilled in the art to satisfy the objectives defined herein. The essential parts to carry out the inventive methods within this particular embodiment are: a means of imposing a compaction stress on the bulk material using centrifugal forces, a means of removing confining plates from the cell, a means of imposing a controlled force to fail an arched material by using centrifugal forces, and a means of recognizing the onset of failure by passing a light signal through the cell. Alternative devices and methods for satisfying the inventive concepts are contemplated and will be obvious to those skilled in the art.

Various other arrangements of light sources and sensors and light paths are contemplated and will be obvious to accomplish the same desired functions as that shown. It should be noted that with the illustrated configuration, the sensor 120 may be independently mounted or fixed to the arm 101. If independent, the potential delay from the powder failure to light detection by the sensor 120 will not alter the results as there will be no significant change in speed in the interim.

Based on the embodiment shown, it will be obvious that the applied acceleration forces may be generated in other ways, although rotational movement is most convenient in most test settings. Likewise, alternative devices and methods of covering and exposing the cavity outlets may be used in substitution of the retaining plates 81, 82 while providing the same function.

All of these devices and steps may be controlled by a computer. This method could be automated, making it user friendly and technician resistant. The parts of this process that lend themselves to computer automation are control of the motors, rotational speed measurement, failure light trigger, environmental control, and calculation of the strength and consolidation pressure. This could be implemented using a laptop computer, simple data acquisition board, and a motor driver board that can accept a voltage input signal. The filling of the test cell and the removal of the retaining plates are best done manually. The footprint for this fully automated device could easily fit on a bench top.

For the most part, the elements in the patent are sequential in nature. Sample preparation should precede filling the cell, and consolidation must always precede testing the material to failure. However, there are some cases where preparing the sample could be skipped as part of the process. The mode of measuring the rotational speed generally includes a non-contact form of measurement. This could include reflectance methods directed toward the shaft, or monitoring proximity sensors placed near the rotating arm. In another embodiment, the detected light that signals failure is used as a trigger to observe and measure rotational speed.

The light source 110 can be any (monochromatic, laser, or multi-frequency) source with sufficient power to be observed either visually or with a photosensitive sensor capable of sensing 10,000 hertz signals. The method of directing the light source through the cell as described above uses a reflecting surface on of a portion of the test cell rotation arm. However, in other embodiments, the mode of directing the light through the cell may use any set of reflective surfaces which eventually direct the light source through the cell either forward or backward.

The inventive test methods could include conditioning the environment (temperature or relative humidity) to a prescribed temperature/humidity profile during the consolidation phase of the test, thereby allowing the tester to mimic actual process conditions.

Figure 4:
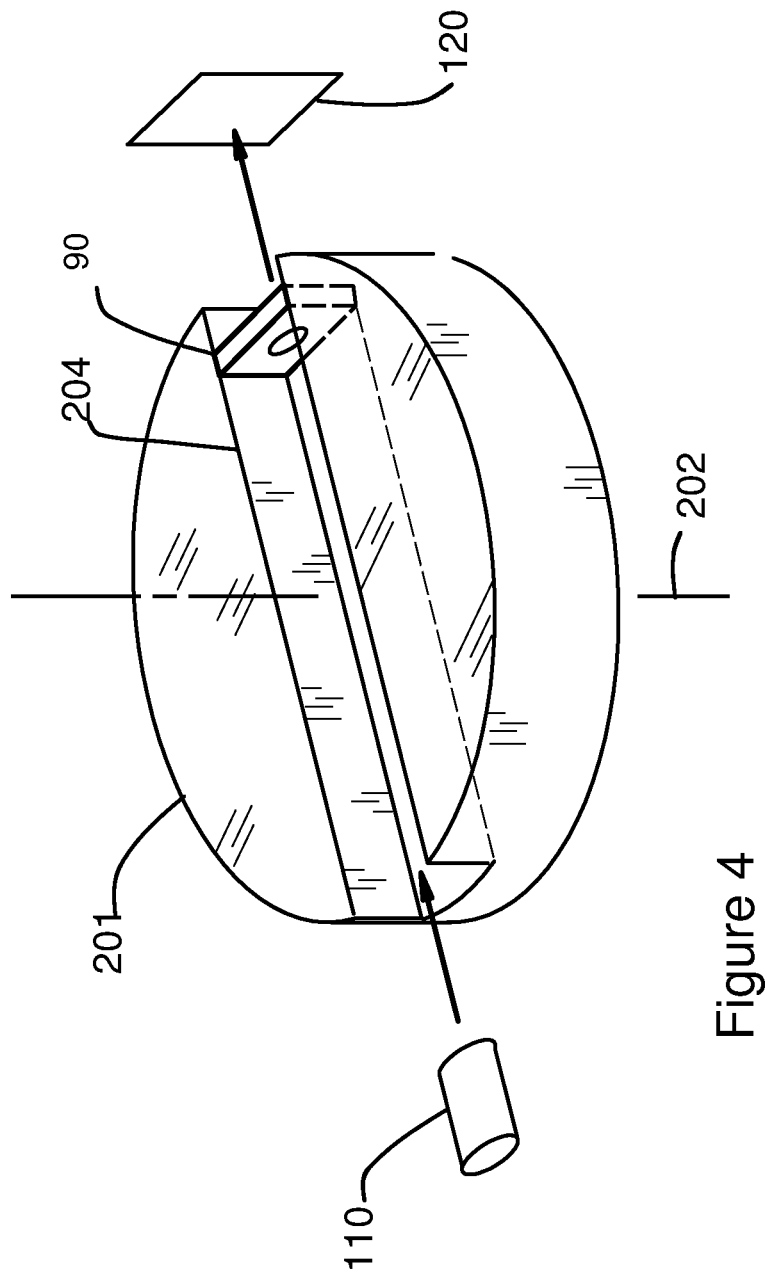
FIG. 4 is a perspective illustration of an alternative configuration of the inventive test device.

FIG. 4 depicts a preferred configuration of a test device for carrying out the process described above. In place of the arm 101, a spindle 201 supports the cell 90 a radial distance from the spindle's vertical axis 202. The spindle has a horizontal open slot 204 aligned with the cell 90 such that a light beam can pass across or through the spindle 201 and through the cell cavity in a manner similar to that described previously. To enable this, a light source 110 is located outside the cell 90 and oriented to direct light through the slot when it is appropriately aligned. A sensor 120 is located and oriented to receive and detect any light so passing through the cell 90. This configuration may be operated in the same manner as that shown in, and described with respect to, FIGS. 2 and 3. The spindle 201 is shown in simplistic form without supporting or other obvious operational features.

It should be clear that although the spindle 201 is depicted as generally cylindrical in shape, this is not limiting and is for convenience of fabrication and balancing. Other shapes and configurations would be equally applicable for the intended purpose. Likewise, the illustrated manner of mounting of the cell 90 is selected for simplicity of balancing and other configurations are possible to provide the essential functions. For example, the cell 90 may be surface-mounted on the top of the spindle 201 if the proper balancing is provided.

The method of detecting the occurrence of powder escaping from the sample in the cell cavity may be carried out in any of a variety of other alternative methods and using other alternative devices and systems. For example, a light beam may be directed across the opening of the cell to detect the passage of powder through the beam. In other alternatives, one or more impact detectors may be placed radially beyond the cell path such that the impinging powder may be detected after leaving the cell cavity. Other alternatives using existing and future technologies are contemplated and may be used for the same or equivalent function and purpose of detecting escape of powder from the call cavity as the devices described above. Likewise, the word "cavity" is used generally to indicate a structure providing the boundary constraint required to contain the sample. Other structures providing the same function are each considered a cavity as the term is used here.

Figure 5:
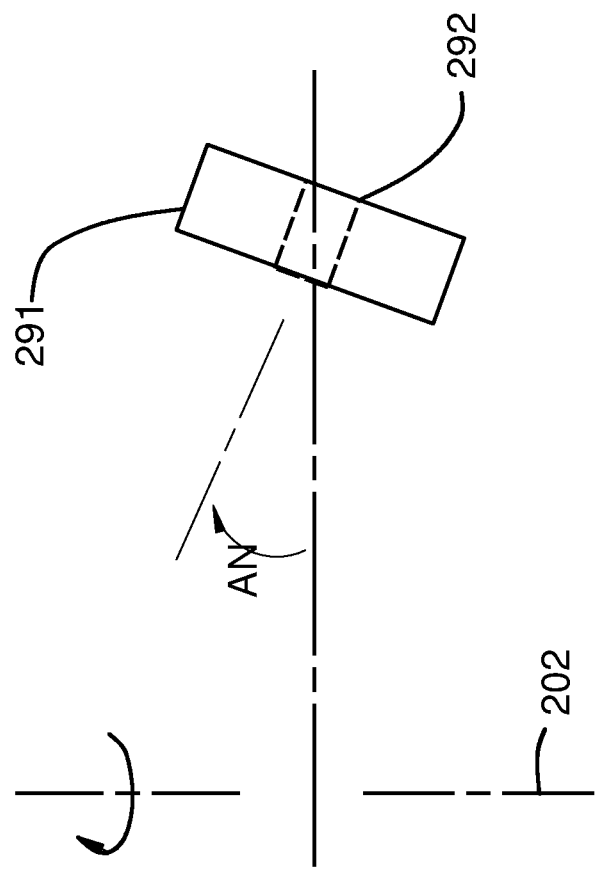
FIG. 5 is a side view of an alternative configuration test fixture for determining the friction angle property of a powder material.

FIG. 5 is a side view of a modified cell 291 that may be used to determine the friction angle of bulk powder materials as a measure of shear strength. The modified cell 291 has a shear cavity 292 having constant square cross section. As described above, the shear cavity 292 is filled with powder and the cell 291 is supported to subjected to radial acceleration forces relative to a vertical rotation axis 202. In this test, the cell 291 is supported (on an arm or spindle) with an included angle AN between the cavity centerline and the horizontal axis, AN being less than 90 degrees. Failure of the bulk powder is determined again by the powder leaving the cell 291 and the light passing through the cell 291 as described previously. The friction angle can be determined by testing at various different angles and finding the minimum angle between the cell center axis and the vertical axis. The true friction angle should be calculated while accounting for the gravitational acceleration in vectorial combination with the applied acceleration. This calculation will be clear to one skilled in the art in light of this disclosure.

Using an alternative configuration of the test cell 291 to that in FIG. 5, a similar powder bulk friction parameter can be measured by rotating the cell about the z-axis (vertical axis) and relative to the direction of the light. This configuration also allows friction angle measurement by vectorial combination of the applied acceleration. In this case the gravitational component remains unchanged since rotation is about the z-axis and the plane of the cell remains vertical. The necessary calculations will also be clear to one skilled in the art.

In methods of determining powder friction angle in the device above, it may be necessary to compact the powder in the cell cavity 292 prior to testing to prevent powder in the cell from spilling out. This may by covering the cavity openings and spinning the cell 291 to provide a compacting acceleration. The cavity 292 would then be uncovered for testing.

Figure 6:
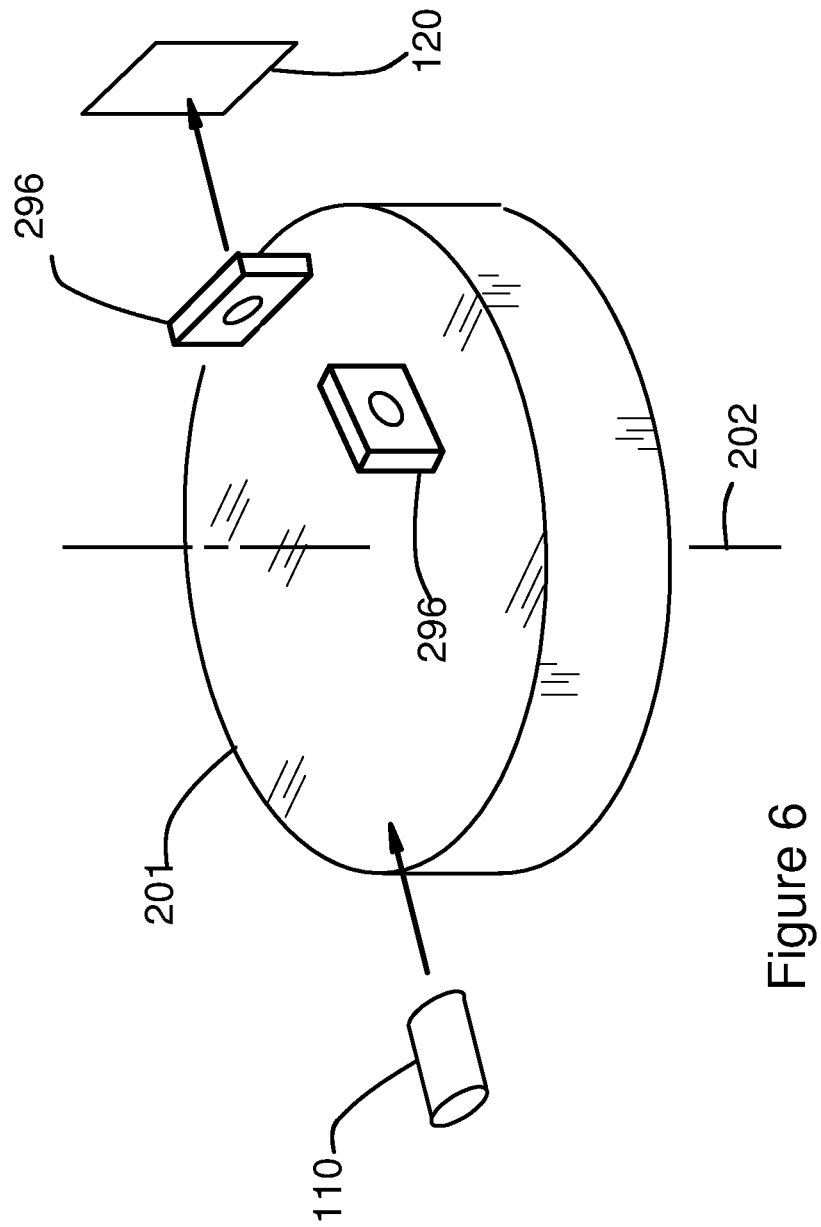
FIG. 6 is a perspective illustration of an alternative test device including multiple test cells.

Because the level of compaction may be a variable of interest, in alternative configurations, multiple cells may be provided located at various different radial distances on a spindle. This is illustrated in FIG. 6 where multiple duplicate cells 296 are located on a common spindle 201. In this manner, a pre-test spinning of the cells will provide a various different acceleration magnitude to each of the duplicate cells 296, with consequent different compaction in each. The compaction forces may be calculated in a known manner from geometry of the spindle, material characteristics and rotational speed. Friction angle may then be determined for each by slowly increasing the rotational speed of the spindle and determining the rotational speed for each cell, and calculating as described above.

Above are described various configurations of inventive devices and methods for determining particular properties of bulk powder materials. Broadly, in the invention a selected bulk powder material property is determined by detecting a defined relationship between externally applied forces applied to the aggregated sample volume of bulk powder and a change in the bulk volume configuration of the powder sample as a consequence of the force applied. The change in sample configuration is defined by and is a product of a relative movement of the aggregate particles within the sample volume. This change in configuration may evidence itself, during the inventive methods, in one of a variety of detectable events depending at least in part on the boundary conditions of the bulk powder sample volume and their spatial relation to the direction of the applied force.

In the first embodiment discussed above, the change in powder sample configuration produced a new, unstable, condition. The consequence and result of the change of sample configuration to an unstable condition was that the bulk powder was forced out of the test cavity due to the applied forces. This final event was used to provide a convenient means of determining the change in configuration that defines the property of interest—in this case the strength of the bulk powder.

By changing the boundary conditions or the nature of the applied force, other useful properties of bulk powder materials may be similarly determined using the essential same device and method or variations applying the same principles.

For example, bulk powder materials typically have flow properties of unconfined yield strength, bulk density, and wall friction angle which are useful to know in industrial applications. These properties can also be expressed in relationships between applied forces and boundary conditions and changes in configuration of bulk powder so constrained and acted upon. The change in configuration may be a relative movement of a portion of the boundary or encompassing surface of the test sample.

In one such example, loose packed bulk powder is placed in container having a small conical cavity and then subjected to acceleration forces to cause the particles of the bulk powder to move closer together as they are compacted against the boundary provided by the cavity. If the acceleration forces are applied in the manner of the embodiments discussed previously, the particles will be forced and compacted radially outward. The total volume of the sample of powder particles will be reduced due to the compaction. This relative movement of the powder particles and associated compaction is a change in sample configuration that can be detected and applied to determine properties of the bulk powder material. The shape of the cavity is not critical and the use of a conical cavity is for convenience. Cavities of other shapes may be used in the same manner.

This configuration change may be detected in any of a variety of possible ways. For example, the position of the top surface of the sample may be monitored through an optical method during the compaction process. The volume of the compacted material can then be computed as a function of the consolidation forces and the bulk density can be determined as a function of the solids contact pressure. One method of monitoring and measuring the top surface position is to place the bulk solid in an optically transparent container and direct a consistent intensity light across the container as it rotates while measuring the intensity of light passing through the container. The measured light intensity is then recorded as a function of rotation speed. This data can be used to infer the relative position of the top compacted surface and compute the bulk density at various compaction stresses.

Figure 7A:
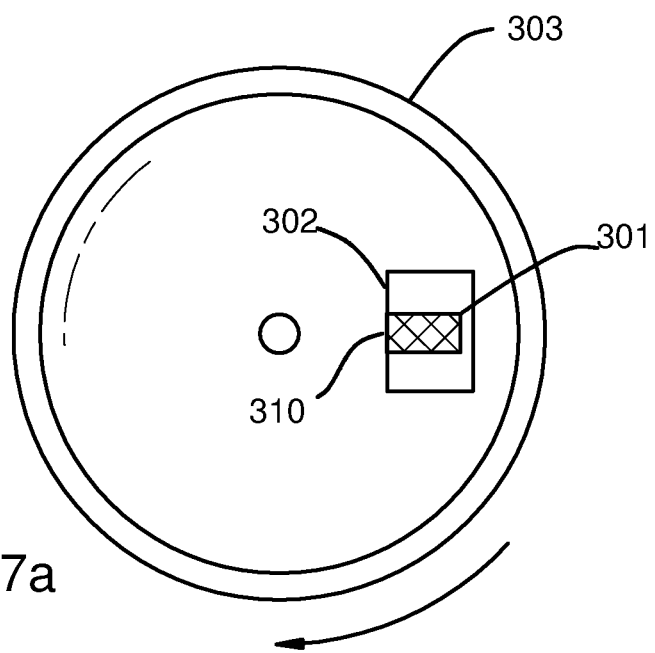
FIGS. 7a and 7b are two different views of the same device for determining density of a powder material according to the invention.
Figure 7B:
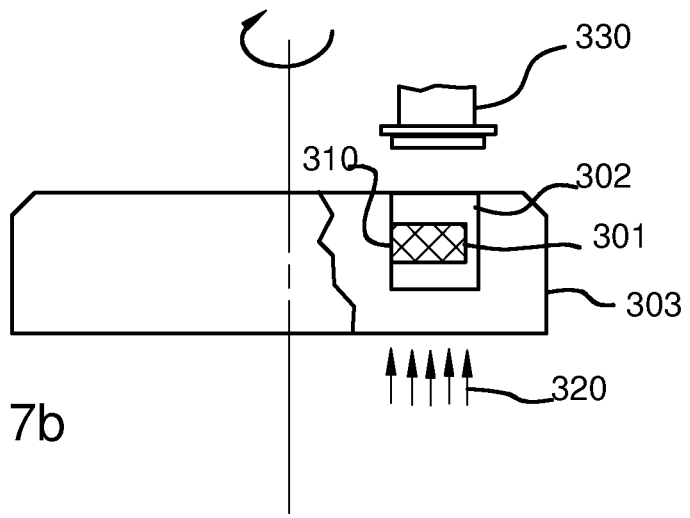

FIGS. 7*a* and 7*b* illustrate the application of a device according to the invention as just described above in determining density of a bulk powder. A hollow cavity 301 is formed in a test cell 302 that is removably secured to a spindle table 303. The cavity 301 in this configuration is cylindrical in shape to demonstrate that, as discussed above, the cavity shape is not critical in this application. The cavity is filled with a sample volume of powder test material 310 the density of which is to be determined. The centerline of the cavity 301 is aligned to pass perpendicularly through the spindle table centerline such that when the spindle table is rotated as indicated, the powder material 310 experiences acceleration forces in a radial outward direction—along the cavity centerline.

A light source is directed to pass light 320 through the volume of powder material 310 and the light that is not obstructed is received and measured by a detector device 330. The test cell 302 must be formed of material that is transparent relative to the applied light form. As well, depending on the configuration and operation of the device, the spindle table, or portions thereof, may be required to be transparent as well. In all cases, any structure surrounding the cavity 301 and located between the light 320 and the detector during detecting must allow light transmission.

The detector 330 should include, or be associated with, functional systems enabling measurement of the transmitted light passing around the cavity 301 in a manner to allow comparative measurements of the light intensity as a function of the area of obstruction created by the volume of the powder material 310. By measuring the light intensity before application of acceleration force, and then after various acceleration forces have compacted the powder material 310 to reduce the volume, and therefore also the cross-sectional area obstructing the light, the density of the powder material under various compaction stress levels may be determined. It should be clear that the light application and measurement steps may be performed while the spindle table is moving or while stationary after operation.

Figure 8:
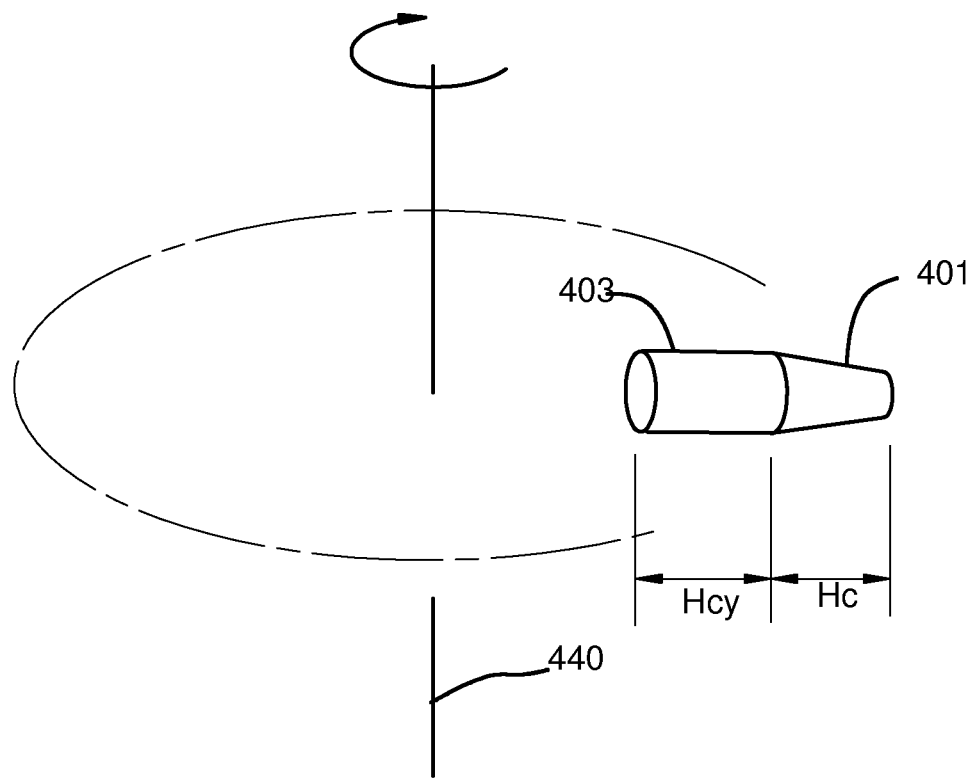
FIG. 8 is a schematic illustration of another method of determining density as a characteristic of a powder material according to the invention.

In an alternative embodiment of the invention used to determine bulk density as a function of compaction pressure, loosely packed bulk powder is placed in a small conical cavity with a small powder-filled cylindrical container connected to it. FIG. 8 illustrates this configuration in schematic form. In the figure, the powder sample 401 is shown without depicting the structure of the confining cavity or any supporting or operating structure. The form and nature of these may generally follow the devices described in the prior embodiments or equivalent alternatives. The sample 401 has a fixed geometry and volume. The centerline of the sample 401 is aligned to cross perpendicularly through a centerline of rotation 440 for the sample 401 as described respecting the configuration in FIG. 7a. Aligned on the sample centerline, and abutting the sample 401 between the sample 401 and the centerline 440 is a second volume 403 of the same powder material. At their adjoining volume faces, the sample 401 and second volume 403 have the same cross-section.

By spinning the sample 401 together with the second volume 403, and thereby applying centrifugal acceleration forces to both, the sample powder particles will be forced to move closer together in an outward radial direction and result in radial compaction of the sample 401, and also movement of powder particles from the second volume 403 into the volume previously filled by the sample 401. This change in configuration is a consolidation and compaction of powder in the sample volume, resulting in a greater aggregate weight occupying the fixed sample volume defined by its cavity structure (not shown). After compaction, the material in the fixed cavity can be isolated from the excess material in the second volume and the weight of powder in the sample volume (the conical cavity) may be determined by conventional means to then calculate the density of the compacted powder as a function of compaction pressure. The conical shape of the cavity and sample volume is not critical but selected for convenience and other shapes may be used with equal effect. As well as providing "makeup" volume of powder particles to the sample volume, the second volume 403 provides additional compacting force to the sample 401 due to the added mass and therefore acceleration force, thereby amplifying the resultant compaction.

The below equations have been found useful in determining strength properties of powdered materials tested using the embodiment shown in FIG. 8 and discussed above. Consolidation stresses (Sigma as previously discussed) can be calculated by the following equation:

$$\text{Sigma} = 4\pi^2 \times K\text{val} \times R \times (\text{RPM}_{comp})^2 \times \text{Density} \times (H_c \times Db^2 + H_c \times Db \times Dt + H_c \times Dt^2 + 3Hcy \times Dt^2)/(3Db^2)$$

The respective bulk unconfined yield strength (Strength) may be then calculated from the equation:

$$\text{Strength} = 2\pi^2 \times K\text{val2} \times R \times (Dt^2 + Db \times Dt + Db^2) \times (\text{RPM}_{fail})^2 \times \ldots \text{Density}/(3Db \times \cos\phi)$$

As shown in the figures, Hc is the axial height of the conical sample 401, while Hcy is the axial height of the second volume 403. The Kval and Kval2 factors may be initially taken as equal to the values 0.882 and 3.25, respectively, and adjusted, based on test data, to calibrate test equipment and accommodate effects of particle size and other variables. The remaining variables in the equations are the same as specified for the prior equations provided above for Sigma and Strength.

Other methods can be used to characterize unconfined strength properties of bulk materials. Each method may give a slightly different value of unconfined strength. It may be advantageous in particular applications to correlate the values obtained from the inventive test methods provided here with those of other test methods or other data. This may be especially useful when large data bases have been previously acquired using other devices and methods. The Kval and Kval2 terms above provide flexibility to modify the above computation to correlate data generated with prior existing data.

In the methods described above, the step of acceleration force determination is distinct from calculating or determining the desired property of the powder. In alternative configurations, devices are contemplated in which acceleration forces are an inherent factor determining the desired property, but the acceleration or acceleration force is not independently measured and recorded. In such configurations, acceleration forces are considered to be determined, and these alternative devices and methods are equal means of carrying out the invention.

It should be clear that the same general method and devices as described above may be used to determine other similar properties of bulk powder materials. Modifying the cavity shape or orientation or other operational parameters of the inventive device or method, while determining a change in powder configuration, such as a disruptive failure, under acceleration in like manner, may be used respecting other properties or process-dependent variables.

The invention claimed is:

1. A method of determining a property of a bulk powder material, comprising;
   confining a sample of powder material within a cavity;
   applying acceleration forces to the sample;
   detecting a configuration change within the sample;
   determining an acceleration force applied at the time of the configuration change; and
   determining a powder property from the acceleration force applied at the time of the configuration change.

2. A method, according to claim 1, and wherein:
   the step applying acceleration forces to the sample comprises rotating the sample about an axis.

3. A method, according to claim 1, and wherein:
   the step of detecting a configuration change comprises measuring a sample property.

4. A method, according to claim 3, and wherein:
   the step of measuring a sample property comprises measuring a sample boundary location.

5. A method, according to claim 3, and wherein;
   the step of measuring a sample property comprises weighting the sample.

6. A method. according to claim 3, and wherein:
   the step of measuring a sample property comprises,
   projecting light past the sample and receiving the passing light with a detector such that the sample obstructs a portion of the light passing; and
   detecting a change in light impinging on the detector due to a change in the size of the sample.

7. A method, according to claim 1, and wherein:
   the step of determining an acceleration force comprises calculating force from a rotational speed of the sample.

8. A method, according to claim 1, and wherein:
   the step of detecting a configuration change of the sample occurs during the step of applying acceleration forces.

9. A method, according to claim 1, and wherein:
the step of detecting a configuration change within the sample occurs during the step of determining an acceleration force applied at the time of the configuration change occurs.

10. A method, according to claim 1, and wherein:
the step of detecting a configuration change within the sample occurs after applying acceleration forces to the sample.

11. A method, according to claim 1, and wherein:
the step of detecting a configuration change within the sample comprises detecting powder material leaving the cavity.

12. A method, according to claim 1, and wherein:
the step of detecting powder material leaving the cavity comprises detecting a light beam passing through the cavity.

13. A method, according to claim 1, and wherein:
the step of detecting powder material leaving the cavity comprises detecting the event of the obscuring of a light beam by the powder material leaving the cavity.

14. A method of determining a property of a bulk powder material, comprising;
disposing a sample of powder material within a cavity;
applying acceleration forces to the sample by spinning the sample about an axis;
detecting a configuration change within the sample; and
determining a powder property using applied acceleration forces.

* * * * *